(12) United States Patent
Nielsen et al.

(10) Patent No.: US 8,038,906 B2
(45) Date of Patent: Oct. 18, 2011

(54) PROCESS FOR THE PREPARATION OF SYNTHESIS GAS FROM BLACK LIQUOR

(75) Inventors: Poul Erik Højlund Nielsen, Fredensborg (DK); Bodil Voss, Virum (DK)

(73) Assignee: Haldor Topsøe A/S, Lyngby (DK)

( * ) Notice: Subject to any disclaimer, the term of this patent is extended or adjusted under 35 U.S.C. 154(b) by 361 days.

(21) Appl. No.: 12/431,240

(22) Filed: Apr. 28, 2009

(65) Prior Publication Data

US 2009/0282739 A1    Nov. 19, 2009

(30) Foreign Application Priority Data

May 16, 2008   (DK) ................................ 2008 00686

(51) Int. Cl.
*D21C 11/00*    (2006.01)
*C10J 3/46*    (2006.01)
*C01B 3/24*    (2006.01)

(52) U.S. Cl. ...................... 252/373; 48/127.1; 48/197 R; 48/204; 423/650

(58) Field of Classification Search ............... 48/61, 127.1–127.9, 197 R–214 A; 423/644–656; 252/373; 585/240

See application file for complete search history.

(56) References Cited

U.S. PATENT DOCUMENTS

| 4,808,264 A * | 2/1989 | Kignell | ........................ 162/30.1 |
| 2004/0055716 A1* | 3/2004 | Landalv et al. | .............. 162/30.1 |
| 2009/0199476 A1* | 8/2009 | Taylor | ......................... 48/197 R |

FOREIGN PATENT DOCUMENTS

WO    WO 02/40768 A1    5/2002

* cited by examiner

*Primary Examiner* — Wayne Langel
*Assistant Examiner* — Syed Iqbal
(74) *Attorney, Agent, or Firm* — Dickstein Shapiro LLP

(57) ABSTRACT

A process for the adjustment of the composition of a synthesis gas produced in a high temperature black liquor gasifier. The process includes the steps of (a) generating a gasifier effluent stream from black liquor in the gasifier by a blast and optionally an atomising stream; (b) optionally quenching the gasifier effluent stream with a gas stream to form a gas quenched effluent stream; (c) quenching the gasifier effluent of step (a) or the gas quenched effluent gas stream of step (b) with a water stream to form a raw synthesis gas; (d) further cooling and cleaning and separating the raw synthesis gas to form a purified unprocessed synthesis gas with an appropriate $H_2/CO$ ratio; (e) partly converting the purified synthesis gas to dimethyl ether in a synthesis section, producing at least a product stream of DME and a hydrogen rich purge stream of processed; (f) splitting and recycling individual or combinations of split streams of the processed or the unprocessed synthesis gas to step a and/or step (b); and recycling a by-product stream of $CO_2$ being further generated in step (e) in part or completely to step (a) and/or step (b).

3 Claims, 1 Drawing Sheet

PROCESS FOR THE PREPARATION OF SYNTHESIS GAS FROM BLACK LIQUOR

BACKGROUND OF THE INVENTION

1. Field of the Invention

This invention relates to a process for preparation of synthesis gas from black liquor gasifiers to be useful in a downstream synthesis. In particular, the invention concerns gasification of black liquor in a high temperature, downflow type gasifier to a synthesis gas stream with improved composition for use in the synthesis of valuable chemicals, especially DME.

2. Description of the Related Art

Synthesis gas can be prepared by gasification of so called black liquor (BL) by means of a blast i.e. oxygen, oxygen enriched air or air.

BL is an intermediate product stream from papermaking processes. It results from cooking of e.g. wood chips with aqueous sodium hydroxide and subsequent reduction in water through evaporation to a water content of about 70% by weight. The BL substance is rich in hemicellulose and lignin and has a relatively high content of inorganic material, forming large amounts of melts during the gasification process.

The known BL gasifier furnace types are constructed in different ways. To this end the gasifiers have either upflow or downflow of the gaseous reaction medium in the gasification chamber and are operated with more or less addition points of blast. In low-temperature BL gasifier types (~600° C. gasification exit temperature) ash is withdrawn as a dry solid rather than a melt. In high-temperature BL gasifier types (~900-1050° C. gasification exit temperature) the inorganic material originating from the BL leaves the gasifier as a liquid melt, which is quenched in a down-stream section.

In the high temperature downflow gasifier, the black liquor is normally supplied through burner means. In the gasification zone exothermic oxidation and endothermic disintegration reactions of the organic substances take place. The resulting temperature from the gasification process is typically about 900-1050° C.

The synthesis gas produced from the organic material dissolved in BL is rich in hydrogen, carbon monoxide and carbon dioxide. The synthesis gas contains additionally water, inert components depending on the composition of the black liquor and oxygen feed and sulphur components together with ash melt of $Na_2CO_3$ and NaS or equivalents of potassium salts.

In this type of gasifier the effluent from the gasification process is usually cooled by quenching with liquid water being sprayed into a quench chamber beneath the gasification chamber.

The melt is thus dissolved in the quench water resulting in formation of green liquor which after caustification is ready for dissolving organic material.

The synthesis gas may be purified and used either as fuel or as feed stock for downstream chemical processes.

A typical composition of the black liquor (BL) substance by weight C 36.14%, H 3.50%, O 34.3%, N 0.14%, S 4.80%, Cl 0.24%, Na 18.6% and K 2.02%. The dry mass percentage of the black liquor is about 70 wt %.

The composition of the synthesis gas produced depends on the BL feed composition, its dry mass percentage, the type of blast and BL atomizing streams and their relative flow rates. The synthesis gas composition depends furthermore on the gasifier operating conditions.

The gasifying process substantially disintegrates the organic mass by thermal cracking into e.g. CO, $CH_4$ and by the homogeneous water gas shift reaction $$H_2O + CO \Leftrightarrow H_2 + CO_2 \qquad (1)$$

in further amounts of $H_2$ and $CO_2$.

To this end, it is known that sodium compounds promote the water gas shift reaction (see f. inst. Sealock, L. J. Jr.; Elliott, D.C. in "Development of an advanced water-gas shift conversion system", 4th annual advanced gasification contractors' meeting; 26 Jun. 1984; Morgantown, W. Va., USA).

Whereas the homogeneous shift reaction is slow at the temperatures prevailing in the quench section of the BL gasifier, the shift reaction due to its promotion by Na compounds may take place down to 250-300° C. Although it will be very slow below 400° C.

In the Lurgi Dry Ash Gasification process raw synthesis gas from a downstream process water cooler is recycled in a split stream to the gasifier for the provision of lock pressurizing gas in order to avoid dilution of the synthesis gas with inert gases.

In the Shell Coal Gasification Process and in the Prenflo Process a split stream of hot quench gas (about 250-280° C.) from a downstream slag filter is recycled to the gasifier to quench cool the effluent.

None of these processes result in changes of the composition of resulting raw synthesis gas.

As mentioned above the composition of the synthesis gas generated by the BL gasification depends e.g. on the gasifier feed compositions and operating conditions. Typically, the $H_2$/CO ratio in the synthesis gas produced from BL gasification is in the range 0.85-1.5, varying over time as the BL feed will vary naturally e.g. with respect to atomic composition, energy content and rheology. The water content in the BL varies as a result of operating changes in the pulp manufacture. Also, there will be an upper limit on the practicable dry mass percentage of BL amongst other setting a limit to how low a ratio of $H_2$/CO ratio can be obtained in the synthesis gas produced from the process.

Conventionally steam is used as the atomising stream in BL gasifiers, because it is readily available at the gasifier pressure (generated on site). An atomising stream is not strictly required, but has a great impact on the efficiency of the gasifier. A minimum flow rate of the atomising stream is about 0.05 kg/kg BL.

In the production of chemical compounds from synthesis gas it is usually necessary to adjust the composition of the gas in order to be useful in the production. Surplus of any reactant will result in additional requirements to the product separation. Especially, where the product is difficult to separate from unreacted components the separation will become prohibitively expensive rendering the process economically unviable.

Increasing interest has been shown to dimethyl ether (DME) over the last decades. DME is an environmentally benign chemical with a wide range of applications. DME can be used as a propellant, as a substitute for LPG in house hold apparatuses and as diesel fuel.

DME is produced from synthesis gas at a pressure typically in the range of 20-100 bar and at temperatures between 200 and 350° C. in one or more beds of catalyst/s promoting the following reactions:

$$4H_2 + 2CO \Leftrightarrow 2CH_3OH \qquad (2)$$

$$H_2O + CO \Leftrightarrow H_2 + CO_2 \qquad (3)$$

$$2CH_3OH \Leftrightarrow CH_6O + H_2O \qquad (4)$$

$$3H_2 + 3CO \Leftrightarrow CH_6O + CO_2 \qquad (2)+(3)+(4)$$

The appropriate $H_2/CO$ mole ratio in the synthesis gas for production of DME is about 1, preferably 0.9 to 1.25.

Downstream or integrated in the DME synthesis section, produced DME and by-product $CO_2$ may be separated from the stream of unconverted synthesis gas, while a purge gas stream lean in CO and $CO_2$, however, typically richer in $H_2$ and inerts is sent to e.g. a fired heater or an auxiliary boiler as fuel.

With the high volatility of DME the efficiency of the synthesis process is sensitive to large variations of the $H_2/CO$ ratio in BL generated synthesis gas.

If the BL gasifier shall provide synthesis gas for use chemical processes, it will usually be necessary to adjust the gas composition independent of the pulp manufacture and the characteristics of the resulting BL to provide an optimal synthesis gas composition.

Thus, it is the general object of this invention to provide a process for the preparation of synthesis gas with an appropriate composition for use in the production of chemical compounds independent of the pulp manufacture and the BL characteristics.

Depending on the raw synthesis gas composition as it is produced in the BL gasifier, it will be necessary either to increase or decrease the $H_2/CO$ ratio in the raw gas to reach at the appropriate ratio.

SUMMARY OF THE INVENTION

It has now been found that the recirculation of processed or unprocessed synthesis gas produced in a BL gasifier to an intermediate zone between the gasification chamber and the quench zone of the gasifier provides an adjusted synthesis gas with an improved composition.

The BL gasifier type being most useful for use in the invention is the high temperature, downflow type fed by BL, a blast and optionally support streams for atomising BL droplets and for obtaining sufficient mixing in the oxidation zone.

Pursuant to the above finding, this invention provides a process for the adjustment of the composition of a synthesis gas produced in a high temperature downflow black liquor gasifier, comprising the steps of
 (a) generating a gasifier effluent stream from black liquor in said gasifier by means of a blast and optionally an atomising stream;
 (b) optionally quenching the gasifier effluent stream with a gas stream to form a gas quenched effluent stream;
 (c) quenching the gasifier effluent of step (a) or the gas quenched effluent gas stream of step (b) with a water stream to form a raw synthesis gas;
 (d) further cooling and cleaning and separating the raw synthesis gas to form a purified unprocessed synthesis gas with an $H_2/CO$ mole ratio of between 0.9 to 1.25;
 (e) partly converting the purified synthesis gas to dimethyl ether in a synthesis section, producing at least a product stream of DME and a hydrogen rich purge stream of processed synthesis gas; and
 (f) splitting and recycling individual or combinations of split streams of the processed synthesis gas from the synthesis section or the unprocessed synthesis gas to step (a) and/or step (b).

The term "unprocessed synthesis gas" refers to synthesis gas, which not yet has been subjected to DME conversion and which is recycled step (a) or (b) from a location upstream to step (e).

Cooling and condensation/dissolution of the ash required for the recovery of green liquor from the BL gasifier is conventionally conducted in a quench zone immediately underneath the gasification chamber of the gasifier.

Recirculation of synthesis gas from downstream synthesis gas split points will contribute to the reduction of $H_2/CO$ ratio in the resulting synthesis gas by suppressing the shift reaction promoted by the alkali melt in the quench zone.

It is furthermore possible to reduce the $H_2/CO$ ratio in the resulting synthesis through recirculation of by-produced $CO_2$ separated from down stream DME synthesis.

Optionally part of the synthesis gas/$CO_2$ is used as atomising stream in the feed section of the gasifier where normally steam is applied. Thus in one embodiment the recirculation of unprocessed synthesis gas or a stream from the downstream DME synthesis reduces the $H_2/CO$ in the resulting synthesis gas by allowing to feed less steam to the gasification chamber.

In some cases the adjustment needed is an increase of the $H_2/CO$ ratio in the raw synthesis gas. In these cases, the raw synthesis gas can be adjusted by increasing the content of hydrogen through recirculation of unconverted synthesis gas purged from a downstream DME synthesis. Optionally, part of the recycled hydrogen rich purge gas may be used as an atomising stream, whereby the normal atomising stream e.g. steam or $CO_2$ may be reduced.

Thus, in further an embodiment of the invention, recirculation of a purge stream rich in hydrogen from a downstream DME synthesis increases the $H_2/CO$ ratio in the resulting synthesis gas. This results further in a decrease of the amounts of steam and/or $CO_2$ to be fed into the gasification chamber.

The synthesis gas purge stream rich in hydrogen is enriched in methane as well. As the gasification of the methane contained in the purge gas contributes also to the moles of synthesis gas produced, advantageously more synthesis gas is produced.

Furthermore, recirculation of both unprocessed synthesis gas prior to the gas is introduced into the synthesis reactor and $CO_2$ will provide a higher reduction of the $H_2/CO$ ratio than recirculation of solely one of these streams.

As it can be understood, the above mentioned means can be combined in any manner for the control of the $H_2/CO$ ratio in the resulting synthesis gas.

BRIEF DESCRIPTION OF THE DRAWINGS

The above features will be explained in more detail in the following examples and by reference to the drawings in which.

DETAILED DESCRIPTION OF THE PREFERRED EMBODIMENTS

Examples

Comparative Example 1

Figure 1:
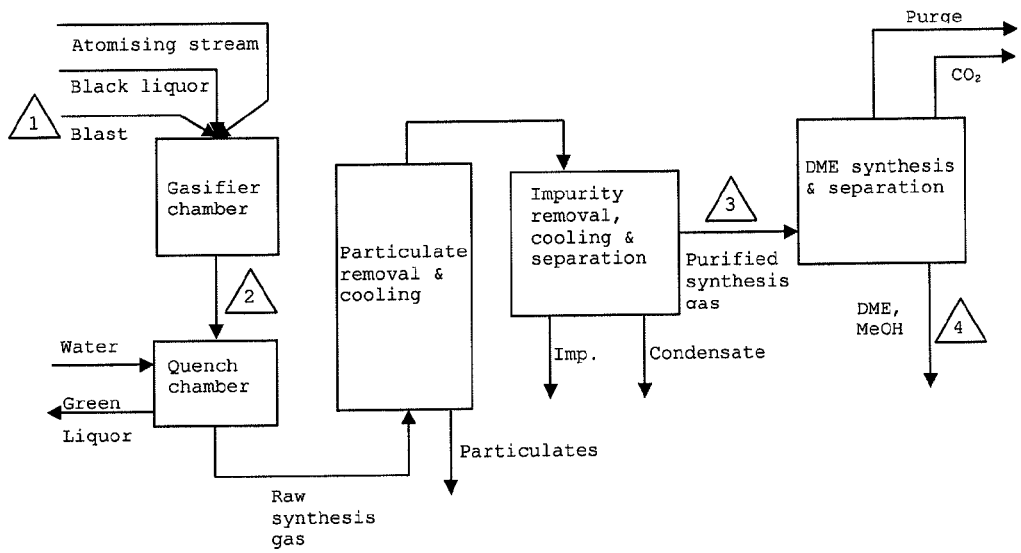
FIG. 1 shows a flow scheme of a conventional process for the preparation of synthesis gas in a BL gasifier for use in a subsequent DME synthesis.

Reference is made to FIG. 1 in the drawings, which shows a conventional process layout of a BL gasifier front end with a down stream purification/cooling and a further down stream dimethyl ether synthesis section. In this process layout, $CO_2$ is separated from the synthesis prior to the DME synthesis section.

1000 kg/h of 70 wt & dry mass (30 wt % water) black liquor with the atomic (weight based) composition C 36.14%, H 3.50%, O 34.3%, N 0.14%, S 4.80%, Cl 0.24%, Na 18.6% and K 2.02% (LHV=3200 kcal/kg) is fed to a black liquor gasifier (35 bar), wherein it is atomised by means of atomising stream of steam being fed at a rate of 0.1 kg steam/kg black liquor and gasified by means of a blast containing 99 vol % oxygen and 1 vol % argon. The blast is adjusted to result in a gasifier effluent temperature of 1000° C. and a methane leakage of 1.81% $CH_4$ on a dry basis.

The gasifier effluent is quenched by means of quenching water to form green liquor, which is recycled to a pulp section.

Raw synthesis gas produced is withdrawn from the quench section and passed to a purification and cooling section.

In the quench section sodium promoted conversion of CO into $H_2$ by the water gas shift reaction proceeds down to a temperature of 923° C. with a 50° C. approach to equilibrium giving a $H_2$/CO ratio of the purified synthesis gas of 1.5. The synthesis gas is compressed and converted in a DME synthesis loop with a recycle-to-make-up ratio of 1 and an exit temperature of the DME synthesis of 260° C. resulting in a DME production rate of 131 kg/h. In this example, the $H_2$/CO ratio in the synthesis gas is outside the optimal ratio for use in DME production.

The key parameters of the above process as shown in FIG. 1 are summarized in Table 1 below, wherein "Position" refers to the various position numbers in FIG. 1.

TABLE 1

| | Position | | | |
|---|---|---|---|---|
| Description | 1<br>Blast | 2<br>Gasifier<br>Effluent | 3<br>Purified<br>synthesis gas | 4<br>DME/MeOH |
| Flow rate, Kmole/h | 9.14 | 51.4 | 30.75 | 3.11 |
| Pressure, barg | 37 | 35 | 31 | 10 |
| Temperature, Deg C. | 300 | 1000 | 30 | 30 |
| Composition, Mole % | | | | |
| Oxygen | 99 | 0 | 0 | 0 |
| Hydrogen | 0 | 23.3 | 40.57 | 0 |
| Carbon Monoxide | 0 | 17.16 | 27.02 | 0 |
| Carbon Dioxide | 0 | 16.98 | 29.72 | 0 |
| Methane | 0 | 1.28 | 2.14 | 0 |
| Nitrogen | 0 | 0.07 | 0.11 | 0 |
| Argon | 1 | 0.18 | 0.3 | 0 |
| Dimethyl Ether | 0 | 0 | 0 | 83.48 |
| Methanol | 0 | 0 | 0 | 16.52 |
| Water | 0 | 38.92 | 0.14 | 0 |
| Impurities | | Bal | — | — |
| $H_2$/CO | | 1.36 | 1.50 | |
| DME eq. rate, kg/h | | | | 131 |

DME eq. rate is given as = $MW_{DME}$ ($n_{DME}$ + $n_{MeOH}$/2), where $n_i$ is the molar flow rate of component i.

Comparative Example 2

Example 1 is repeated with the exception that the atomising stream has been reduced to a rate of 0.05 kg/kg black liquor. The $H_2$/CO ratio in the purified synthesis gas is 1.39 and the DME production is increased to 135 kg/h due to the decreased $H_2$/CO ratio in the synthesis gas.

Table 2 below summarizes the key parameters of this example by reference to FIG. 1.

TABLE 2

| | Position | | | |
|---|---|---|---|---|
| Description | 1<br>Blast | 2<br>Gasifier<br>Effluent | 3<br>Purified<br>synthesis gas | 4<br>DME/MeOH |
| Flow rate, Kmole/h | 8.92 | 48.36 | 30.32 | 3.17 |
| Pressure, barg | 37 | 35 | 31 | 10 |
| Temperature, Deg C. | 300 | 1000 | 30 | 30 |
| Composition, Mole % | | | | |
| Oxygen | 99 | 0 | 0 | 0 |
| Hydrogen | 0 | 23.82 | 39.68 | 0 |
| Carbon Monoxide | 0 | 18.99 | 28.58 | 0 |
| Carbon Dioxide | 0 | 17.01 | 28.58 | 0 |
| Methane | 0 | 1.63 | 2.61 | 0 |
| Nitrogen | 0 | 0.07 | 0.11 | 0 |
| Argon | 1 | 0.18 | 0.29 | 0 |
| Dimethyl Ether | 0 | 0 | 0 | 84.7 |
| Methanol | 0 | 0 | 0 | 15.3 |
| Water | 0 | 36.02 | 0.14 | 0 |
| Impurities | | Bal | — | — |
| $H_2$/CO | | 1.25 | 1.39 | |
| DME eq. rate, kg/h | | | | 135 |

Example 3

Figure 2:
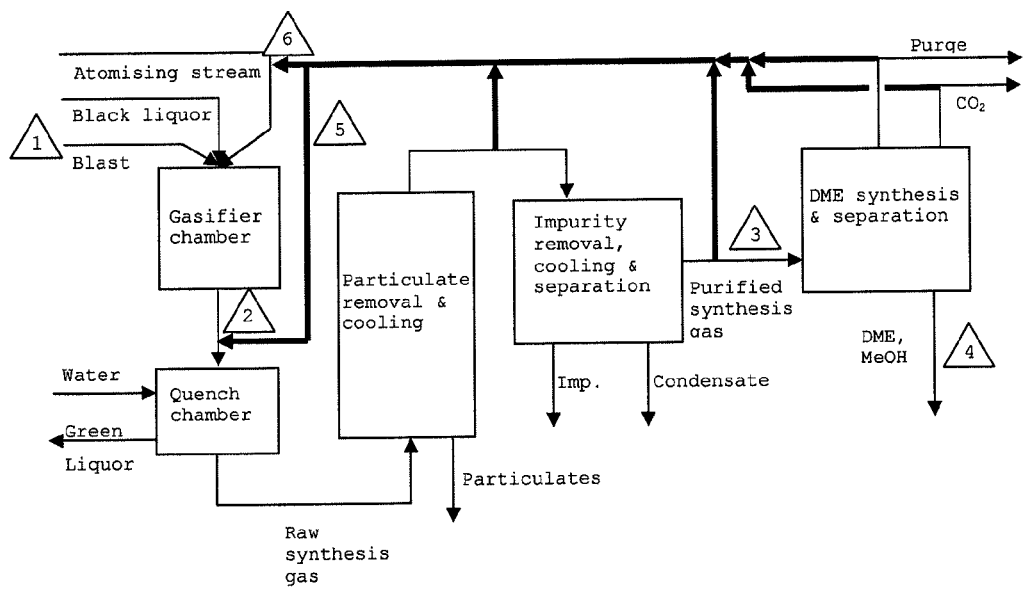
FIG. 2 is a flow scheme of the process according to the invention.

This is an example of the invention demonstrating the impact of recycling unprocessed synthesis gas to a BL gasifier. Reference is made to FIG. 2 in the drawings.

Example 2 is repeated, with the exception that a split stream of purified synthesis gas is recycled to an addition point between the gasifier chamber and the quench chamber of the gasifier. Thereby, the gasifier effluent is cooled by quench with the recycled synthesis gas to a temperature of 923° C. prior to the effluent is further quenched with water.

The effect obtained when recycling raw/purified synthesis gas is that the conditions for the promotion of the water gas shift conventionally present in the quench section are eliminated, thus leaving the $H_2$/CO ratio in the synthesis gas closer to its optimum for use in the down stream conversion to dimethyl ether. The $H_2$/CO ratio of the purified synthesis gas is in this example 1.25 and the DME production is increased to 141 kg/h.

Table 3 below summarizes the key parameters used and obtained in the example with reference to FIG. 2.

TABLE 3

| | Position | | | | |
|---|---|---|---|---|---|
| Description | 1<br>Blast | 2<br>Gasifier<br>effluent | 3<br>Purified<br>synthesis<br>gas | 4<br>DME/<br>MeOH | 5<br>Gas<br>quench |
| Flow rate, Kmole/h | 8.92 | 48.36 | 29.81 | 3.29 | 4.66 |
| Pressure, barg | 37 | 35 | 31 | 10 | 35 |
| Temperature, Deg C. | 300 | 1000 | 30 | 30 | 43 |
| Composition, Mole % | | | | | |
| Oxygen | 99 | 0 | 0 | 0 | 0 |
| Hydrogen | 0 | 23.82 | 38.63 | 0 | 38.63 |
| Carbon Monoxide | 0 | 18.99 | 30.8 | 0 | 30.8 |
| Carbon Dioxide | 0 | 17.01 | 27.37 | 0 | 27.37 |
| Methane | 0 | 1.63 | 2.65 | 0 | 2.65 |
| Nitrogen | 0 | 0.07 | 0.12 | 0 | 0.12 |
| Argon | 1 | 0.18 | 0.3 | 0 | 0.3 |
| Dimethyl Ether | 0 | 0 | 0 | 86.29 | 0 |
| Methanol | 0 | 0 | 0 | 13.71 | 0 |
| Water | 0 | 36.02 | 0.14 | 0 | 0.14 |
| Impurities | | Bal | — | — | — |

TABLE 3-continued

| | Position | | | | |
|---|---|---|---|---|---|
| | 1 | 2 | 3 | 4 | 5 |
| $H_2/CO$ | | 1.25 | 1.25 | | |
| DME eq. rate, kg/h | | | | 141 | |

Example 4

The example demonstrates the effect of recycling purge gas from a down stream DME synthesis to a BL gasifier.

Example 3 is repeated with the exception that a BL stream with a higher dry matter percentage of 80 wt % is fed to the gasifier. Such variation results in a gasifier effluent being lower in $H_2/CO$ ratio than optimal for the DME synthesis. The split stream of purge gas from the DME synthesis section is used as the gas quench. The temperature of the quenched gasifier effluent is 523° C. Due to the surplus of hydrogen in the purge gas stream from the DME synthesis section the $H_2/CO$ ratio of the resulting purified synthesis gas to the DME synthesis section is then close to 1, which is optimal stoichiometric ratio. The DME production is 148 kg/h.

Table 4 shows the key parameters describing used and obtained in the example with reference to FIG. 2.

TABLE 4

| | Position | | | | |
|---|---|---|---|---|---|
| | 1 | 2 | 3 | 4 | 5 |
| Description | Blast | Gasifier Effluent | Purified synthesis gas | DME/ MeOH | Gas quench |
| Flow rate, Kmole/h | 7.46 | 39.53 | 31.37 | 3.32 | 2.99 |
| Pressure, barg | 37 | 35 | 31 | 10 | 35 |
| Temperature, Deg C. | 300 | 1000 | 30 | 30 | 42 |
| Composition, Mole % | | | | | |
| Oxygen | 99 | 0 | 0 | 0 | 0 |
| Hydrogen | 0 | 25.46 | 34.49 | 0 | 25.29 |
| Carbon Monoxide | 0 | 26.46 | 34.6 | 0 | 13.35 |
| Carbon Dioxide | 0 | 15.65 | 20.56 | 0 | 9.72 |
| Methane | 0 | 3.94 | 9.55 | 0 | 48.08 |
| Nitrogen | 0 | 0.09 | 0.21 | 0 | 1.08 |
| Argon | 1 | 0.19 | 0.46 | 0 | 2.31 |
| Dimethyl Ether | 0 | 0 | 0 | 93.29 | 0 |
| Methanol | 0 | 0 | 0 | 6.71 | 0 |
| Water | 0 | 25.43 | 0.14 | 0 | 0.17 |
| Impurities | | Bal | — | — | — |
| $H_2/CO$ | | 0.96 | 1.00 | | |
| DME eq. rate, kg/h | | | | 148 | |

Example 5

This is an example demonstrating the effect of a recycle of $CO_2$ separated from a down stream DME synthesis to a BL gasifier. Example 3 is repeated, but instead of raw/purified synthesis gas $CO_2$ is recycled as a gas quench, which means that the $H_2/CO$ ratio in the gasifier effluent is adjusted at a value of 1.25 and the production rate of DME is 142 kg/h.

Table 5 below summarizes the key parameters used and obtained in the example with reference to FIG. 2.

TABLE 5

| | Position | | | | |
|---|---|---|---|---|---|
| | 1 | 2 | 3 | 4 | 5 |
| Description | Blast | Gasifier effluent | Purified synthesis gas | DME/ MeOH | Gas quench |
| Flow rate, Kmole/h | 8.92 | 48.36 | 35.51 | 3.32 | 6.1 |
| Pressure, barg | 37 | 35 | 31 | 10 | 35 |
| Temperature, Deg C. | 300 | 1000 | 30 | 30 | 42 |
| Composition, Mole % | | | | | |
| Oxygen | 99 | 0 | 0 | 0 | 0 |
| Hydrogen | 0 | 23.82 | 32.43 | 0 | 0 |
| Carbon Monoxide | 0 | 18.99 | 25.86 | 0 | 0 |
| Carbon Dioxide | 0 | 17.01 | 39 | 0 | 93.82 |
| Methane | 0 | 1.63 | 2.22 | 0 | 0 |
| Nitrogen | 0 | 0.07 | 0.1 | 0 | 0 |
| Argon | 1 | 0.18 | 0.25 | 0 | 0 |
| Dimethyl Ether | 0 | 0 | 0 | 85.49 | 0 |
| Methanol | 0 | 0 | 0 | 14.51 | 0 |
| Water | 0 | 36.02 | 0.14 | 0 | 6.18 |
| Impurities | | bal | — | — | — |
| $H_2/CO$ | | 1.25 | 1.25 | | |
| DME eq. rate, kg/h | | | | 142 | |

Example 6

This example demonstrates the effect of recycling part of the purge gas from a down stream DME synthesis to the BL gasifier as both a gas purge stream and an atomising stream.

Example 4 is repeated with the exception that a second split stream of purge gas is used as an atomising stream in stead of steam at a rate of 0.05 kg/kg Black liquor.

Part of the methane contained in the purge stream is thence gasified in the gasifier, increasing the amount of hydrogen and carbon monoxide in the gasifier effluent stream. The resulting $H_2/CO$ ratio is 1.00 and the production rate of DME is 149 kg/h.

Table 6 below summarizes the key parameters used and obtained in the example with reference to FIG. 2.

TABLE 6

| | Position | | | | | |
|---|---|---|---|---|---|---|
| | 1 | 2 | 3 | 4 | 5 | 6 |
| Description | Blast | Gasifier effluent | Purified synthesis gas | DME/MeOH | Gas quench | Atomising gas |
| Flow rate, Kmole/h | 6.55 | 38.91 | 31.53 | 3.32 | 2.92 | 2.52 |
| Pressure, barg | 37 | 35 | 31 | 10 | 35 | 35 |
| Temperature, Deg C. | 300 | 1000 | 30 | 30 | 42 | 42 |

TABLE 6-continued

| | Position | | | | | |
|---|---|---|---|---|---|---|
| | 1 | 2 | 3 | 4 | 5 | 6 |
| Composition, Mole % | | | | | | |
| Oxygen | 99 | 0 | 0 | 0 | 0 | 0 |
| Hydrogen | 0 | 26.45 | 34.95 | 0 | 24.96 | 24.96 |
| Carbon Monoxide | 0 | 27.36 | 35.01 | 0 | 13.43 | 13.43 |
| Carbon Dioxide | 0 | 14.52 | 18.74 | 0 | 9.65 | 9.65 |
| Methane | 0 | 4.9 | 10.6 | 0 | 49.19 | 49.19 |
| Nitrogen | 0 | 0.09 | 0.19 | 0 | 0.9 | 0.9 |
| Argon | 1 | 0.17 | 0.36 | 0 | 1.7 | 1.7 |
| Dimethyl Ether | 0 | 0 | 0 | 93.34 | 0 | 0 |
| Methanol | 0 | 0 | 0 | 6.66 | 0 | 0 |
| Water | 0 | 23.69 | 0.14 | 0 | 0.17 | 0.17 |
| Impurities | | Bal | — | — | — | — |
| $H_2/CO$ | | 0.97 | 1.00 | | | |
| DME eq. rate, kg/h | | | | 149 | | |

What is claimed is:

1. A process for the adjustment of the composition of a synthesis gas produced in a high temperature downflow black liquor gasifier, comprising the steps of (a) generating a gasifier effluent stream from black liquor in said gasifier by means of a blast and optionally an atomising stream;

(b) optionally quenching the gasifier effluent stream with a gas stream to form a gas quenched effluent stream;

(c) quenching the gasifier effluent of step (a) or the gas quenched effluent gas stream of step (b) with a water stream to form a raw synthesis gas;

(d) further cooling and cleaning and separating the raw synthesis gas to form a purified unprocessed synthesis gas with an $H_2/CO$ ratio of between 0.9 and 1.25;

(e) partly converting the purified synthesis gas to dimethyl ether in a synthesis section, producing at least a product stream of DME and a hydrogen rich purge stream of processed synthesis gas;

(f) splitting and recycling individual or combinations of split streams of the processed synthesis gas from the synthesis section or the unprocessed synthesis gas to step (a) and/or step (b), wherein a by-product stream of $CO_2$ being further generated in step (e) is in part or completely recycled to step (a) and/or step (b).

2. A process of claim 1, wherein the by-product stream of $CO_2$ is recycled together with the processed or the unprocessed synthesis gas.

3. A process of claim 1, wherein the unprocessed synthesis gas is recycled to step (a) as the atomising stream.

* * * * *